US011382499B2

(12) United States Patent
Brocwell et al.

(10) Patent No.: US 11,382,499 B2
(45) Date of Patent: Jul. 12, 2022

(54) REMOTE EYE EXAMINATION SYSTEM

(71) Applicant: VPH INTELLECTUAL PROPERTY, LLC, Palm Springs, FL (US)

(72) Inventors: Christopher Bradley Brocwell, Waynesville, OH (US); Alvaro Jose Moreno Hernandez, Boca Raton, FL (US); Daniel Scott Stanton, Palm Springs, FL (US)

(73) Assignee: VPH INTELLECTUAL PROPERTY, LLC, Palm Springs, FL (US)

( * ) Notice: Subject to any disclaimer, the term of this patent is extended or adjusted under 35 U.S.C. 154(b) by 392 days.

(21) Appl. No.: 16/248,577

(22) Filed: Jan. 15, 2019

(65) Prior Publication Data

US 2019/0216312 A1    Jul. 18, 2019

Related U.S. Application Data

(60) Provisional application No. 62/617,533, filed on Jan. 15, 2018.

(51) Int. Cl.
*A61B 3/028* (2006.01)
*G16H 10/60* (2018.01)
(Continued)

(52) U.S. Cl.
CPC .......... *A61B 3/0285* (2013.01); *A61B 3/0033* (2013.01); *A61B 3/028* (2013.01); *G08B 5/36* (2013.01); *G16H 10/60* (2018.01); *G16H 40/67* (2018.01); *G16H 80/00* (2018.01); *H04L 41/0681* (2013.01); *H04L 65/1069* (2013.01)

(58) Field of Classification Search
CPC .. A61B 3/00; A61B 3/02; A61B 3/032; A61B 3/0285; A61B 3/0033; A61B 3/028; A61B 3/024; A61B 3/036; A61B 3/066; A61B 3/0041; A61B 3/0091; A61B 3/0025; G16H 40/67; G16H 10/60; G16H 80/00; G08B 5/36; H04L 41/0681; H04L 65/1069; H04L 29/06; H04L 12/24
USPC ....... 351/235, 237, 239, 203, 208, 222, 223, 351/243–246
See application file for complete search history.

(56) References Cited

U.S. PATENT DOCUMENTS

| 2003/0210378 A1* | 11/2003 | Riza | A61B 3/066 351/205 |
| 2011/0082704 A1* | 4/2011 | Blum | A61B 3/0285 705/2 |
| 2019/0013960 A1* | 1/2019 | Sadwick | H05B 47/155 |

* cited by examiner

Primary Examiner — Jie Lei
(74) Attorney, Agent, or Firm — Shutts & Bowen LLP

(57) ABSTRACT

A remote eye examination method includes initiating a remote chat session between a local computing device coupled to a phoropter, and a remote computer, and initializing the phoropter for remote control by the remote computer. Then, a multi-colored lamp is activated in a first color until a determination that a refractory examination utilizing the phoropter has commenced. Thereafter, responsive to a determination that the examination has commenced, the multi-colored lamp changes to a second color, and movement of portions of the phoropter are commanded as directed by the remote computer, data is recorded into a patient record and a progression of the examination monitored. Finally, on condition that a threshold period of time before a conclusion of the refractory examination is detected, the multi-colored lamp changes to a third color and upon conclusion of the examination, a message transmitted to a remote account indicating access to the patient record.

5 Claims, 1 Drawing Sheet

(51) Int. Cl.
*H04L 29/06* (2006.01)
*G08B 5/36* (2006.01)
*H04L 12/24* (2006.01)
*A61B 3/00* (2006.01)
*H04L 41/0681* (2022.01)
*H04L 65/1069* (2022.01)
*G16H 80/00* (2018.01)
*G16H 40/67* (2018.01)

REMOTE EYE EXAMINATION SYSTEM

BACKGROUND OF THE INVENTION

Field of the Invention

The present invention relates to the field of telemedicine and more particularly to a remote eye examination system and methodology.

Description of the Related Art

A patient's access to eye care has long been an issue in small towns and remote areas across the U.S. (and across the world). Patients who are able to drive, are sometimes force to travel hundreds of miles for eye care. Unfortunately, those who lack the ability to drive such long distances often go without care. Tragically, this not only affects adults but numerous children as well. Poor vision in children can lead to visual developmental delays which, if untreated, can result in permanent vision loss. Furthermore, it is estimated that up to 80% of a child's learning is done visually—putting those who do not have access to eye care at a major disadvantage.

Historically, eye care could only be performed if an eye care provider had a doctor physically on location. This meant if there was not a doctor locally, the doctor would have to travel to the location to provide services. This resulted in inconsistent coverage, as such coverage was dependent of the ability of the doctor to consistently travel to such physical locations. It also resulted in a lack of continuity of care for many patients. In other cases, eye care was only accessible through long, expensive trips to provide one-time care to remote areas and countries. This created issues with accessibility to care in small areas, remote areas, and countries without access to care.

According to Global Eyesight Now, the global economic cost of lost work productivity due to people with poor vision has been estimated at 700 billion dollars a year. Refractive error, which eyeglasses correct, is the number one cause of vision impairment in the world. It is also the second greatest cause of preventable blindness. 6 out of 10 people in the developed world wear glasses, contact lenses, or have had corrective eye surgery. 6 out of 10 people in the developing world are also vision impaired, but have little or no access to eye care or eyeglasses. In North America, the ratio of optometrists to people is approximately 1:6,000. By comparison, in sub-Saharan Africa, the ratio of optometrists to people i s approximately 1:8,000,000.

Even in the United States, metropolitan areas create issues with supply and demand, with the demand for eye care professionals and eye care being much greater than the supply. Again, even in the United States, if a physical location could not staff a doctor or if the doctor called out sick or was on vacation, patients could not be seen and would have to be cancelled or rescheduled.

BRIEF SUMMARY OF THE INVENTION

Embodiments of the present invention address deficiencies of the art in respect to remote eye examination and provide a novel and non-obvious method, system and computer program product for a remote eye examination system. In an embodiment of the invention, a system and method for remotely performing eye examinations (hereinafter the "Remote Eye Examination System" or "REES") is a system and method for providing telemedicine services which allows for increased accessibility for patient eye care. REES addresses the need to have a doctor on location to administer eye care. Using REES, doctors now have the ability to, using an intuitive refractive software, delegate the physical refraction examination to an unskilled, non-professional and have confidence they such non-professional provide the patient with accurate, reliable information to diagnosis and treat the patient's refractive error.

REES addresses the rising cost of eye care. In smaller facilities, there may not be sufficient volume to keep an optometrist fully occupied. Thus, optometrists in traditional facilities often waste time, waiting in between patient appointments. The REES Telemedicine enables fractional optometrist employment. By offering telemedicine appointments, providers can utilize the amount of their unused capacity which would otherwise go to waste. REES allows eye care providers to start or stop accepting patients based upon their current availability. As this capacity would otherwise not produce any revenue, eye care providers are able to invoice remote patient visits at a lower billing rate than what such providers would normally offer. This, in turn, reduces system costs by enabling patients to receive care at a lower price point. Telemedicine also enables eye care providers with multiple physical locations to better distribute staff throughout such physical locations and to load-balance resources across entire systems—reaching more patients with less strain on optometrists and ophthalmologists.

REES allows for a team of remote doctors, licensed in multiple states or countries, to provide care remotely, creating more consistent coverage that is not dependent on local doctor coverage or availability. REES also enables one doctor to provide eye care services for multiple locations at the same time and over long distances. Other tele-medicine platforms require licensed staffed to perform remote refractions. REES' intuitive refractive software allows non-licensed staff to perform accurate and consistent refractions since the REES software makes the "decisions" for such non-licensed staff based on a multitude of patient responses. Moreover, unlike other refractive platforms which have no person-to-person interaction in a non-professional setting, REES provides a "warm, inviting and professional" interaction directly with a refractionist runs the REES software in a professional setting.

In an embodiment of the invention, a remote eye examination method includes initiating a remote chat session over a computer communications network between a local computing device coupled to a remotely controlled phoropter, and a remote computer and initializing the phoropter for remote control by the remote computer. The method additionally includes activating a multi-colored lamp in a first color until a determination is made that a refractory examination utilizing the phoropter has commenced for a specific patient. Thereafter, responsive to a determination that the refractory examination utilizing the phoropter has commenced, the method includes changing the multi-colored lamp to a second color, commanding movement of portions of the phoropter as directed by the remote computer, recording data into a patient record of the specific patient and monitoring a progression of the refractory examination. Finally, on condition that a threshold period of time before a conclusion of the refractory examination is detected, the method includes changing the multi-colored lamp to a third color and thereafter, upon conclusion of the refractory examination, transmitting a message to a remote account indicating access to the patient record.

In one aspect of the embodiment, the remote control is enabled through remote support software executing in the local computing device. In another aspect of the embodiment, the method additionally includes pre-populating the patient record with pre-examination data resulting from each of lensometry; ARK; Tonometry; visual fields; and retinal photography. In yet another aspect of the embodiment, the method additionally includes displaying in a second remote computer, a status of the refractory examination. Finally, in even yet another aspect of the embodiment, on condition that a remote chat session is unable to be initiated, the method includes displaying an alert in a display of the second remote computer.

In another embodiment of the invention, a remote eye examination system (REES) includes a local computing device coupled to a remotely controlled phoropter disposed in a patient examination room and communicatively coupled to a remote computer from over a computer communications network. The system also includes a multi-colored lamp mounted on a wall outside of the patient examination room. Finally, the system includes a remote refractory module. The module includes computer program instructions executing in memory of the local computing device and enabled to perform initiating a remote chat session over the computer communications network between the local computing device and the remote computer, initializing the phoropter for remote control by the remote computer, activating the multi-colored lamp in a first color until a determination is made that a refractory examination utilizing the phoropter has commenced for a specific patient, responding to a determination that the refractory examination utilizing the phoropter has commenced by changing the multi-colored lamp to a second color, commanding movement of portions of the phoropter as directed by the remote computer, recording data into a patient record of the specific patient and monitoring a progression of the refractory examination, and, on condition that a threshold period of time before a conclusion of the refractory examination is detected, changing the multi-colored lamp to a third color and thereafter, upon conclusion of the refractory examination, transmitting a message to a remote account indicating access to the patient record.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Traditional refraction had to been done by a licensed optometrist or ophthalmologist located onsite directly controlling the phoropter. The REES software allows the phoropter to be controlled at a remote location by a refractionist through a simple and user friendly interface controlled by a complex and intuitive algorithm which assists & prompts the operator to ask questions to a patient, then intuitively make complex decision on the patient's refractive error based on the patient's responses. Then, the refractive data is telemetered to a server, from which a remote doctor reviews such data and finalizes the prescription.

Figure 1:
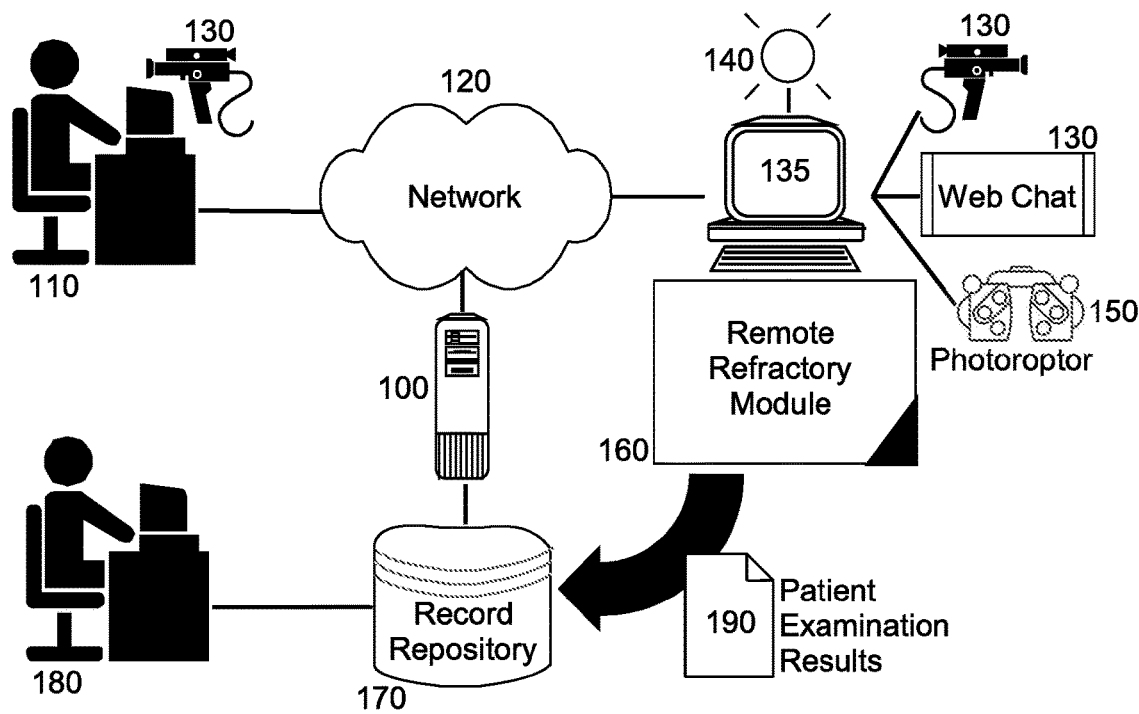
FIG. 1 is schematic illustration of a REES.

In further illustration, FIG. 1 is schematic illustration of a REES. As shown in FIG. 1, a remote refractionist 110 is communicatively linked to a local computing device 135 from over a computer communications network 120. The local computing device 135 which includes memory and at least one processor, hosts the execution of remote refractory module 160 and a Web chat system 130. Of note, a remotely controlled phoropter 150 is coupled to the local computing device 135 as is a multi-colored light 140. The remotely controlled phoropter 150 is adapted to be remotely controlled by remote refractionist 110 over the computer communications network 120, for example, through the operation of a remote desktop session or other such remote support software executing in the local computing device 135. The multi-colored light 140 in turn is operable to change colors responsive to different events such as in response to the initialization of the phoropter 150, the commencement of a refractory examination, the computation that the end of the refractory examination is imminent based upon a state of an examination conducted using the phoropter 150, and an emergency condition during the refractory examination.

Importantly, the remote refractory module 160 includes computer program instructions that when executing in the local computing device 135, is operable to initiate a Web chat session with the remote refractionist 110 using the Web chat system 130, to initialize remote access to the phoropter 150 by the remote refractionist 110 and the activate a green color in the multi-colored lamp 140. The program instructions further are enabled to detect a commencement of a refractory examination utilizing the photoroptor 150 and to activate a yellow color in the multi-colored lamp 140 in consequence. The program instructions yet further are operable to monitor a progression of the refractory examination and to detect when a threshold period of time remains in the refractory examination, in response to which an orange color is activated in the multi-colored lamp 140. Finally, the program instructions are operable to transmit examination results 190 of the refractory examination to a record repository 170 accessible by a remote practitioner 180 by way of a remote server 100 from over the computer communications network 120.

Figure 2:
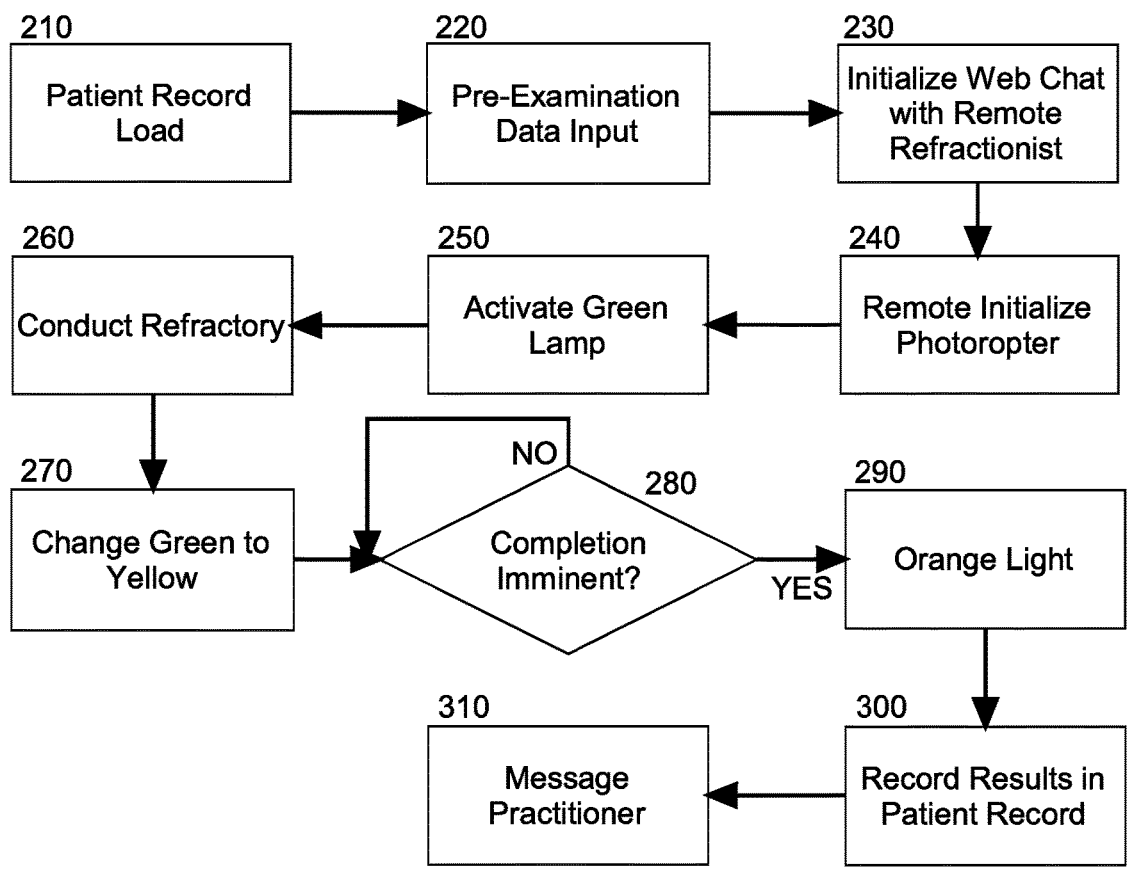
FIG. 2 is a flow chart illustrating a process for performing a remote eye examination using the REES of FIG. 1.

In yet further illustration of the operation of the remote refractory module 160, FIG. 2 is a flow chart illustrating a process for performing a remote eye examination using the REES of FIG. 1. Beginning in block 210, a patient record is loaded for a patient and in block 220, data input resulting from a pre-examination in a local facility is added to the patient record through Web form based input. The pre-examination includes lensometry; ARK; Tonometry; visual fields; and retinal photography. The patient record is then provided to the remote refractionist in block 230 as a Web chat is initiated with the remote refractionist.

In block 240, the phoropter initializes and in block 250 the multi-color lamp is set to green. The refractory examination commences in block 260 in response to which the color of the multi-color light is changed to yellow in block 270. In decision block 280 it is determined if the refractory examination is nearing completion. If so, in block 290 the color of the multi-color lamp is changed to orange. Finally, upon completion of the refractory examination, in block 300 the results of the refractory examination are added to the patient record and in block 310, the patient record is provided to a remote practitioner.

The remote practitioner may then review the patient record via a remote Web interface to REES and determine an appropriate diagnosis and treatment plan. The practitioner may then confirm the record or request further testing of the patient (including referring the patient for further testing with either an in-house or outside doctor). The remote practitioner also can directly edit the corresponding prescription for the patient, make recommendations to the patient, give the patient educational information, etc. Inside the local facility, the staff has a queue of patients waiting to be refracted which allows them to check the status of their patient during the process. (i.e., in progress, action required, signed off, referral, etc.).

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are pos- sible without departing from the scope of the invention defined in the appended claims as follows:

We claim:

1. A remote eye examination system (REES) comprising:
   a local computing device coupled to a remotely controlled photoropter disposed in a patient examination room and communicatively coupled to a remote computer from over a computer communications network;
   a multi-colored lamp mounted on a wall outside of the patient examination room; and,
   a remote refractory module comprising computer program instructions executing in memory of the local computing device, the program instructions performing:
   initiating a remote chat session over the computer communications network between the local computing device and the remote computer;
   initializing the photoropter for remote control by the remote computer;
   activating the multi-colored lamp in a first color until a determination is made that a refractory examination utilizing the photoropter has commenced for a specific patient;
   determining that the examination has commenced upon detecting initialization of the photoropter and responsive to a determination that the refractory examination utilizing the photoropter has commenced, changing the multi-colored lamp to a second color, commanding movement of portions of the photoropter as directed by the remote computer, recording data into a patient record of the specific patient and monitoring a progression of the refractory examination; and,
   on condition that a pre-specified period of time before a conclusion of the refractory examination is detected, changing the multi-colored lamp to a third color and thereafter, upon conclusion of the refractory examination, transmitting a message to a remote account indicating access to the patient record.

2. The system of claim 1, wherein the remote control is enabled through remote support software executing in the local computing device.

3. The system of claim 1, wherein the program instructions are further enabled to perform pre-populating the patient record with pre-examination data resulting from each of lensometry; Tonometry;
   visual fields; and retinal photography.

4. The system of claim 1, wherein the program instructions are further enabled to perform displaying in a second remote computer, a status of the refractory examination.

5. The system of claim 4, wherein on condition that a remote chat session is unable to be initiated, the program instructions perform displaying an alert in a display of the second remote computer.

* * * * *